(12) United States Patent
Stuckert et al.

(10) Patent No.: US 11,883,775 B2
(45) Date of Patent: Jan. 30, 2024

(54) RATE/KINETIC SELECTIVE MULTIPLE BED ADSORPTION PROCESS CYCLE

(71) Applicant: PRAXAIR TECHNOLOGY, INC., Danbury, CT (US)

(72) Inventors: Nicholas R. Stuckert, Grand Island, NY (US); Michael St. James, Calgary (CA)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 598 days.

(21) Appl. No.: 17/042,516

(22) PCT Filed: Mar. 28, 2019

(86) PCT No.: PCT/US2019/024571
§ 371 (c)(1),
(2) Date: Sep. 28, 2020

(87) PCT Pub. No.: WO2019/191421
PCT Pub. Date: Oct. 3, 2019

(65) Prior Publication Data
US 2021/0023497 A1    Jan. 28, 2021

Related U.S. Application Data

(60) Provisional application No. 62/649,798, filed on Mar. 29, 2018.

(51) Int. Cl.
*B01D 53/047* (2006.01)
*C10L 3/10* (2006.01)
(Continued)

(52) U.S. Cl.
CPC ....... *B01D 53/047* (2013.01); *B01D 53/0423* (2013.01); *B01J 20/18* (2013.01);
(Continued)

(58) Field of Classification Search
CPC ...... B01D 53/02; B01D 53/04; B01D 53/047; B01D 53/0423; B01D 2253/108;
(Continued)

(56) References Cited

U.S. PATENT DOCUMENTS

| | | |
|---|---|---|
| 2,843,219 A | 7/1958 | Habgood |
| 4,801,308 A | 1/1989 | Keefer |

(Continued)

FOREIGN PATENT DOCUMENTS

| | | |
|---|---|---|
| CN | 105396420 A | 3/2016 |
| CN | 205575628 U | 9/2016 |

(Continued)

OTHER PUBLICATIONS

Ackley, M. W et al., "Adsorption Characteristics of High-Exchange Clinoptilolites", Industrial & Engineering Chemistry Research, vol. 30, No. 12, Dec. 30, 1991, pp. 2523-2530, XP000274307, ISSN: 0888-5885, DOI: 10.1021/e00060A004 point "B. Pore Volume", p. 2527-2528, Figure 5.

(Continued)

*Primary Examiner* — Frank M Lawrence, Jr.
(74) *Attorney, Agent, or Firm* — Ralph J. Mancini (57) ABSTRACT

The present invention is directed to an intensified process cycle that utilizes the adsorption beds present to a substantially greater degree allowing the processing of significantly more gas and/or the generation of significantly more product. The elimination of purge steps, reduction in equalization step times, and introduction of overlapping feed and equalization steps which normally cause a degradation in performance for equilibrium-based cycles, frees extra step for other actions to be taken, such as additional equalization steps, etc.

19 Claims, 11 Drawing Sheets

(51) Int. Cl.
*B01J 20/18* (2006.01)
*C07C 7/12* (2006.01)
*B01D 53/04* (2006.01)

(52) U.S. Cl.
CPC ............ *B01J 20/186* (2013.01); *C07C 7/12* (2013.01); *C10L 3/105* (2013.01); *B01D 2253/108* (2013.01); *B01D 2256/10* (2013.01); *B01D 2256/16* (2013.01); *B01D 2256/245* (2013.01); *B01D 2257/102* (2013.01); *B01D 2257/104* (2013.01); *B01D 2257/504* (2013.01); *B01D 2259/404* (2013.01); *B01D 2259/40011* (2013.01); *B01D 2259/4062* (2013.01); *C10L 2290/542* (2013.01)

(58) Field of Classification Search
CPC .......... B01D 2253/116; B01D 2253/25; B01D 2253/308; B01D 2256/10; B01D 2256/16; B01D 2256/245; B01D 2257/102; B01D 2257/104; B01D 2257/504; B01D 2259/40011; B01D 2259/404; B01D 2259/4062; B01J 20/18; B01J 20/186; C01B 21/00; C07C 7/12; C10L 3/10; C10L 3/104; C10L 3/105; C10L 2290/542; Y02C 20/40
USPC .............................. 95/96, 130, 138, 139, 148
See application file for complete search history.

(56) References Cited

U.S. PATENT DOCUMENTS

| | | | |
|---|---|---|---|
| 4,816,121 A | 3/1989 | Keefer | |
| 4,964,889 A | 10/1990 | Chao | |
| 4,968,329 A | 11/1990 | Keefer | |
| 5,082,473 A | 1/1992 | Keefer | |
| 5,203,888 A | 4/1993 | Maurer | |
| 5,256,172 A | 10/1993 | Keefer | |
| 5,258,056 A | 11/1993 | Shirley et al. | |
| 5,702,504 A | 12/1997 | Schaub et al. | |
| 6,030,435 A | 2/2000 | Monereau et al. | |
| 6,051,050 A | 4/2000 | Keefer et al. | |
| 6,056,804 A | 5/2000 | Keefer et al. | |
| 6,063,161 A | 5/2000 | Keefer et al. | |
| 6,176,897 B1 | 1/2001 | Keefer | |
| 6,197,092 B1 | 3/2001 | Butwell et al. | |
| 6,231,644 B1 | 5/2001 | Jain et al. | |
| 6,315,817 B1 | 11/2001 | Butwell et al. | |
| 6,406,523 B1 | 6/2002 | Connor et al. | |
| 6,444,012 B1 | 9/2002 | Dolan et al. | |
| 6,629,525 B2 | 10/2003 | Hill et al. | |
| 6,651,658 B1 | 11/2003 | Hill et al. | |
| 6,691,702 B2 | 2/2004 | Appel et al. | |
| 7,179,324 B2 | 2/2007 | Baksh et al. | |
| 7,641,716 B2 | 1/2010 | Lomax, Jr. et al. | |
| 8,778,051 B2 | 7/2014 | Weist, Jr. et al. | |
| 9,381,460 B2 | 7/2016 | Weist, Jr. et al. | |
| 2003/0015091 A1* | 1/2003 | Xu | B01D 53/047 95/96 |
| 2005/0098034 A1 | 5/2005 | Gittleman et al. | |
| 2008/0282884 A1 | 11/2008 | Kelley et al. | |
| 2008/0282892 A1 | 11/2008 | Deckman et al. | |
| 2008/0282899 A1 | 11/2008 | Deckman et al. | |
| 2012/0174775 A1 | 7/2012 | Baksh et al. | |
| 2013/0255492 A1* | 10/2013 | Hsu | C01B 3/56 95/100 |
| 2014/0208797 A1 | 7/2014 | Kelley et al. | |
| 2014/0373713 A1 | 12/2014 | Weist, Jr. et al. | |
| 2016/0097013 A1* | 4/2016 | Knaebel | B01D 53/053 95/102 |
| 2017/0173555 A1 | 6/2017 | Seo | |
| 2018/0229175 A1 | 8/2018 | Pontonio et al. | |

FOREIGN PATENT DOCUMENTS

| | | |
|---|---|---|
| EP | 2663382 B1 | 8/2017 |
| WO | 1999/032222 A1 | 7/1999 |
| WO | 2002/058818 A2 | 8/2002 |
| WO | 2008/005492 A1 | 1/2008 |
| WO | 2012/096812 A1 | 7/2012 |
| WO | 20190191436 A1 | 10/2019 |

OTHER PUBLICATIONS

Mehrotra, et al., Arithmetic Approach for Complex PSA Cycle Scheduling, Adsorption, 2010, pp. 113-126, vol. 16, Springer Science+Business Media.

Yon and Turnock, Multicomponent Adsorption Equilibria on Molecular Sieves, published as part of the AIChE Symposium Series, 117, vol. 67, in 1971 in Adsorption Technology.

Gamba, Giuseppe et al., "Adsorbed Solution Theory Models for Multicomponent Adsorption Equilibria", AIChE Journal, Jun. 1989, vol. 35, No. 6, pp. 959-966.

\* cited by examiner

```
METHOD LOG:
1:SELECT GAS: 1
2:RAMP 1.00°C/MIN TO 25.00°C
3:ISOTHERMAL FOR 20.00 MIN
4:SAMPLING INTERVAL 0.50 SEC/PT
5:SELECT GAS: 2
6:ISOTHERMAL FOR 30.00 MIN
7:SELECT GAS: 1
8:ISOTHERMAL FOR 30.00 MIN
9:SAMPLING INTERVAL 10.00 SEC/PT
10:RAMP 2.00°C/MIN TO 150.00°C
11:ISOTHERMAL FOR 60.00 MIN
12:RAMP 5.00°C/MIN TO 350.00°C
13:ISOTHERMAL FOR 120.00 MIN
14:RAMP 5.00°C/MIN TO 25.00°C
15:ISOTHERMAL FOR 120.00 MIN
16:SAMPLING INTERVAL 0.50 SEC/PT
17:SELECT GAS: 2
18:ISOTHERMAL FOR 30.00 MIN
19:SELECT GAS: 1
20:ISOTHERMAL FOR 30.00 MIN
21:END OF METHOD
```

| 4-1-2-2 | Bed | Step | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|---|
| | 1 | F | F | EQD2 | EQD1/F | X | X | EQD2 | BD | BD | BD | BD | BD | BD | BD | EQD1 | EQD1/F | F |
| | 2 | BD | BD | EQD1 | F | F | F | F | EQD1 | X | X | EQD2 | BD | BD | BD | BD | BD | BD |
| | 3 | BD | BD | BD | BD | BD | BD | EQD2 | EQD1/F | F | F | EQD2 | EQD1/F | X | X | EQD2 | BD | BD |
| | 4 | X | X | EQD2 | BD | BD | BD | BD | BD | BD | BD | EQD2 | EQD1/F | F | F | F | EQD1 | X |

RATE/KINETIC SELECTIVE MULTIPLE BED ADSORPTION PROCESS CYCLE

RELATED APPLICATIONS

This application claims the benefit of International Application No. PCT/US2019/024571, filed on Mar. 28, 2019, and U.S. Provisional Application Ser. No. 62/649,798, filed on Mar. 29, 2018, which is incorporated herein by reference.

FIELD OF THE INVENTION

The present invention generally relates to a process for systems that remove a contaminant from a feed stream primarily through rate or kinetically selective adsorption. These systems differ substantially from typical equilibrium selective adsorption and can be found commercially in nitrogen pressure swing adsorption (PSA) systems. Rate selective carbon molecular sieves are generally known to provide rate selective characteristics that can be exploited in these processes.

Rate selective adsorption with non-equilibrium selective adsorbents requires different considerations than equilibrium selective adsorbents in multi-bed situations. Advances made in equilibrium selective multi-bed system processes were applied to simple rate selective adsorption systems and demonstrated as inferior to for these processes. New considerations however drastically increase the performance of the system and ultimate recovery and economics.

This invention consists of a multibed process for rate selective adsorbents to increase efficiency and recovery of product gases by introducing additional equalization steps, more time to regenerate the system, and/or more beds available at a time to process feed gas not normally present in a PSA system. These additional equalization steps can be enabled by introducing novel rest steps, overlapping equalization and feed pressurization, and omitting purge.

These new cycles were demonstrated on $N_2$ removal from natural gas but apply to any rate selective process that has a non-equilibrium selective adsorbent (defined as an adsorbent that preferentially adsorbs the product rather than the contaminant at equilibrium).

BACKGROUND OF THE INVENTION

No process is exactly the same with the exact same adsorbent and the exact same feed conditions. As such, each process must be evaluated individually, and this can be a monumental task. As an example of the difficultly with making this selection, for a very simple 4 bed, 4 phase cycle there are 38 step options which can be mutually exclusive for only 2 beds at a time. The resulting complexity is 3^(4*4)^ 38 ^ 150 assuming only 1 second variation in step time, up to 150 seconds for a step by varying bed size, which results in roughly 1E59000 combinations, the diameter of the universe is only 1E29 feet. Each simulation can take over 200 hours to reach an optimal cyclic steady state to evaluate the full performance of the cycle. In order to find the optimal it would take roughly 1E58999 years. To this end, finding a cycle or a regime of operating cycles that are useful and a significant increase over current production cycles is non-obvious even to one skilled in the art, and is especially true for new applications or novel adsorbents. Trends that run counter to conventional wisdom can completely rewrite the methodologies and correlations previously discovered. This invention relates to the findings for a very specific process corresponding to rate selective materials.

Adsorption processes such as pressure swing adsorption (PSA), vacuum swing adsorption (VSA) and vacuum pressure swing (VPSA) have been commercially utilized for bulk air separation, as well as trace air contaminant removal, for a few decades. In PSA and VPSA processes, compressed air is pumped through a fixed bed of an adsorbent exhibiting an adsorptive preference for one of the main constituents, typically $N_2$ in bulk air separation, $CO_2$ and $H_2O$ in air prepurification, or CO and $CO_2$ in $H_2$ purification, etc., whereby an effluent product stream enriched in the lesser-adsorbed constituent is obtained. Improvements in these processes remain important goals, one principal means of which is the discovery and development of better process cycles. Significant improvements have been achieved in not only recovery of gas but also reductions in overall system size. These improvements also continue to provide important benefits even while the adsorbent being used to power the system is constantly improved and replaced with better alternatives.

One strategy to increase the recovery of the product gas is the introduction of equalization steps. These steps work to conserve compressed gas in the void spaces that has already been processed and additionally conserve energy through the reduction of pressurization needed for a subsequent bed before it is put into a production step. In an equilibrium selective process, one of the continual improvements sought is the increase in rate of adsorption. Consequently this also increases the rate of desorption. During an equalization step, if the flux through the bed is substantially higher than the adsorption rate of the material, then the adsorption front can spread in the bed during depressurization. This phenomenon does not reverse itself during pressurization and thus the product gas contaminant concentration increases.

There are a number of patents that teach rapid cycle PSA processes, but with significantly reduced first pass recovery. U.S. Pat. No. 6,231,644 to Jain et al. describes an improved air separation process utilizing a monolithic adsorbent material where the cycle time is 35 seconds. U.S. Pat. Nos. 6,176,897 and 6,056,804 to Keefer et al. describe cycle times of less than one second but include varied methods of energy recovery due to very low first pass gas recovery from the adsorbent bed. With a stream that is already compressed to above 10 psig, loss of energy and capital to recover those losses weigh heavily on the benefit of rapid PSA processes.

Baksh et al. in U.S. Pat. No. 7,179,324 describes a multi-step poly bed cycle to produce a purified hydrogen gas. This patent describes the methodology to use a 3-bed multi equalization process that allows for a significant gain in recovery, comparable to adding a 4th bed but without the additional cost. Using a concurrent equalization and feed step is also disclosed but is hampered due to decreased performance. Preference is for a minimum of 11 second steps and a purge step is mandatory.

U.S. Pat. No. 8,778,051 discloses using a concurrent equalization and feed step, but this is not ideal due to decreased performance. A purge step is also mandatory in this process.

U.S. Pat. No. 9,381,460 discloses using a concurrent equalization and feed step, referencing U.S. Pat. No. 8,778,051, which also suffers from decreased performance. As part of the disclosure a timing from 1-150 seconds is disclosed but 10-150 seconds seems to be preferred. A purge step is mandatory in this process.

It is an object of the claimed invention to provide an intensified process cycle that increases productivity and/or recovery of a rate selective adsorbent system, through the introduction of more equalization steps, more time to regenerate the system and/or more beds available at a time to process feed gas.

SUMMARY OF THE INVENTION

The present invention is directed to an intensified process cycle that utilizes the adsorption beds present to a substantially greater degree allowing the processing of significantly more gas and/or the generation of significantly more product. The elimination of purge steps, reduction in equalization step times, and introduction of overlapping feed and equalization steps which normally cause a degradation in performance for equilibrium-based cycles, frees extra step for other actions to be taken, such as additional equalization steps, etc.

DETAILED DESCRIPTION OF THE FIGURES

The legend for FIGS. 1-3 is:
F—feed step and make product if at pressure
EQD1—first equalization down
EQD2—second equalization down
EQD3—third equalization down
X—Idle step
BD—bed blow down/vent
EQU3—third equalization up
EQU2—second equalization up
EQU1/F—first equalization up, overlap feed
PP/F—product pressurization, overlap feed FIG. 4 outlines the TGA method sequence to measure the rates of adsorption of nitrogen and methane.

DETAILED DESCRIPTION OF THE INVENTION

The current invention is a poly bed (>1 bed) system for rate selective adsorption processes. Novel considerations are faster transient steps (equalization and pressurization/depressurization), which enables the inclusion of an overlapping equalization and feed step.

While these characteristics are primarily described for the separation of nitrogen from natural gas, it should be noted that they will apply to other kinetic based separations as well provided that the impurity to be separated from the product gas has the characteristics described for nitrogen and natural gas/methane, respectively.

The process may also include other adsorbents to remove a range of contaminants that are present in the feed stream including hydrocarbons that contain more than 4 carbon atoms, moisture, carbon dioxide, sulfur containing species or other species that may reduce the working capacity of the adsorbent described herein. In one embodiment the PSA process is directed to the separation of $N_2$ from methane, in another embodiment the separation of $CO_2$ from methane, and in yet another embodiment $O_2$ from $N_2$. Other separations are apparent to those skilled in the art. In the event that one of these adsorbents fails to remove the species, thermal regeneration may be performed to remove that species from the adsorbent described and still fall within the realm of this invention which is to eliminate thermal regeneration from being used to remove the product gas of the invention.

In one embodiment adsorbents having crystalline inorganic frameworks are preferentially utilized in accordance with the present invention. Crystalline inorganic adsorbents are defined as any microporous aluminosilicate having a regular arrangement of atoms in a space lattice. Zeolites are a preferred crystalline inorganic framework. Zeolites are porous crystalline aluminosilicates which comprise assemblies of $SiO_4$ and $AlO_4$ tetrahedra joined together through sharing of oxygen atoms. The general stoichiometric unit cell formula for a zeolite framework is:

where M is the cation with a valence of m, z is the number of water molecules in each unit cell, and x and y are integers such that y/x is greater than or equal to 1. The ratio of oxygen atoms to combined aluminum and silicon atoms is equal to 2. Therefore, each aluminum atom introduces a negative charge of one (−1) on the zeolite framework which is balanced by that of a cation. To activate the zeolite the water molecules are completely or substantially removed by raising the temperature or pulling vacuum. This results in a framework with the remaining atoms intact producing cavities connected by channels or pores. The channel size is determined by the number of atoms which form the apertures leading to the cavities as well as cation type and position. Changing the position and type of the cation allows one to change and fine tune channel size and the properties of the zeolite, including its selectivity. For instance, the sodium form of Zeolite A has a pore size of ~4 Å and is called a 4A molecular sieve. If at least 40% of the sodium ions are exchanged with a larger potassium ion, the pore size is reduced to ~3 Å. If these are exchanged with >70% calcium, one calcium ion replaces two sodium ions and the pore opening is increased to ~5 Å. The ability to adjust pores to precisely determine uniform openings allows for molecules smaller than its pore diameter to be adsorbed while excluding larger molecules. The Si/Al ratio can also be varied to modify the framework structure and provide selectivity required for a given separation. This is why zeolites, known as molecular sieves, are very effective in separating on the basis of size.

Some non-limiting examples of zeolites that can be employed in the context of the invention include zeolite A, chabazite, mordenite, clinoptilolite, ZSM-5, or combinations thereof. The above zeolites can be exchanged with cations including Li, Na, K, Mg, Ca, Sr, Ba, Cu, Ag, Zn, NH4+ and mixtures thereof. In one embodiment of the invention Zeolite A also known as 4A is the zeolite of choice.

The intensified process cycle of the invention utilizes the adsorption beds present to a substantially greater degree allowing the processing of significantly more gas and/or the generation of significantly more product. The elimination of purge steps, reduction in equalization step times, and introduction of overlapping feed and equalization steps which normally cause a degradation in performance for equilibrium-based cycles, frees extra step for other actions to be taken, such as additional equalization steps, etc.

In one embodiment the present invention relates to a pressure swing adsorption process for separating a pressurized feed supply gas containing at least one more rapidly adsorbable component and at least one less rapidly adsorbable product gas component which comprises continuous feeding of a supply gas into a feed input end of an adsorber bed containing at least one solid adsorbent which kinetically adsorbs the more rapidly adsorbable component and withdrawing the least rapidly adsorbable component from an exit end of the adsorber bed, which has a at least 2 beds in service in which the continuous feeding of the supply gas sequentially through each of the adsorber beds produces product gas by using continuous feed gas, constant product gas step, a product pressurization step, a high pressure equalization step wherein there is a product make step that overlaps with feeding the bed, at least one equalization up step and one equalization down step, a blow down step to depressurize the bed, wherein there is substantially no purge provided to any bed during any step in the PSA process.

In one embodiment pressure swing adsorption more rapidly adsorbable component is $N_2$ and/or $CO_2$ and the less rapidly adsorbable component is methane.
In yet another embodiment the wherein the product gas or the less rapidly adsorbable component is $N_2$ and the more rapidly adsorbable component is $O_2$.

Overlap Equalization and Feed Pressurization with a Split Step

A primary method for process intensification is through the overlapping of feed and equalization steps. During the first equalization down and the last equalization up, overlap of the equalization up with feed pressurization is a technique to increase the number of beds online at a time during a given cycle and provide for a continuous feed with a 3-bed cycle. Unexpectedly, with a rapid equalization, the majority of the step still delivers the maximum amount of equalization while preserving the continuous feed. What can be seen is that the adsorption rate is too slow for the adsorption front to be significantly affected by rapid equalizations or rapid pressurizations. This is in contrast to equilibrium selective adsorbents where the adsorption rate is too slow. Essentially the majority of equilibrium selective adsorbents are in a regime in which the rates of adsorption are either too fast to prevent the adsorption of the gas phase passing by the particle, or too slow to fully adsorb the contaminants from the gas phase passing by the particle. While this method has been disclosed by others for equilibrium selective processes, it results is a significant degradation of performance. It has not been disclosed for rate selective processes. Here it has been found that the overlapping of these two steps does not negatively impact the performance of the cycle, and additional benefit can then be achieved with a freed step to accomplish another equalization step, more blow down time or by processing more feed gas with an additional bed.

Another area for process intensification is the elimination of a purge step altogether. In an equilibrium selective process, the pressure within the particle is largely at equilibrium with the pressure outside the particle. The driving force to remove adsorbed contaminants is a concentration difference between inside and outside the particle. For this reason, a sweep/purge gas flow across the outside of the particle significantly increases the desorption rate of contaminates. In rate selective processes, the particle is substantially not at a pressure equilibrium with the outside of the particle, that the primary driver of desorption is the pressure within the crystal, rather than the concentration difference. Providing a sweep gas to change the concentration outside the particle provides minimal benefit. Instead using this step to accomplish another task, more greatly benefits the process and the production of the system.

Intensification can also be achieved by the introduction of rest steps. Typically state of the art teaches rest steps are only available in many multi bed systems (above 8). This is due to the front diffusion that is caused by allowing gas to stagnant in an adsorbent bed. Previous practice would teach us to avoid steps in which there is no gas flow in the bed since when a bed is at rest, the gas naturally mixes and diffuses throughout the bed, broadening the adsorption front and reducing the efficiency of the bed. This is so detrimental that the teaching for less than 8 beds has been to not introduce rest steps and instead to make sure gas is always flowing in a PSA system. Counter intuitively by choosing to rest the bed before depressurization/pressurization or while equalizing down/up and using the time gained to introduce an additional equalization step or increase venting time, an unexpectedly superior recovery rate was observed. This is attributed to the theory that the rate of desorption in the adsorbent is slow enough that gas diffusion does not greatly change the concentration front in the adsorption sites. The observation of a benefit to use this step during depressurization and equalizing up likely indicates that the gas being transferred to the 2nd bed has sufficient time to adsorb and increase in purity before the product make step begins. Contrary to high purity selective adsorption systems, the slow rate helps to keep the front from dispersing during rapid gas movement, allowing the front in the adsorbent to be unchanged while the front is the gas phase is moved from one bed to another and rebuilt with product pressurization. Here it is found that due to the slow adsorption and desorption rates of the contaminant and the product, the diffusion of gas provides a negligible difference to the performance of the PSA system. This then enables the introduction of rest steps for systems with 8 or less beds which can lead to the introduction of an additional equalization step or other steps that can greatly increase the productivity of the system.

Another method for intensification is the introduction of ultra-rapid equalization steps that are largely enabled by the same reason as the rest steps which is the resistance to gas diffusion within the adsorbents. In a typical cycle, it is found that gas can pass so quickly from one adsorbent bed to another such that a low purity gas can pass through the high purity regime of the bed, then be followed by a high purity gas and the adsorption front will still be maintained. This is unheard of in equilibrium selective systems due to the rapid adsorption nature of the adsorbents. This finding enables equalization steps that can take as little as 1 second, which are shown to not only decrease the performance of equilibrium selective cycles, but to cause them to be unable to perform as required. This allows cycles to be developed that spend significantly less time on equalization steps and more time processing feed gas and venting waste gas.

Figure 1:
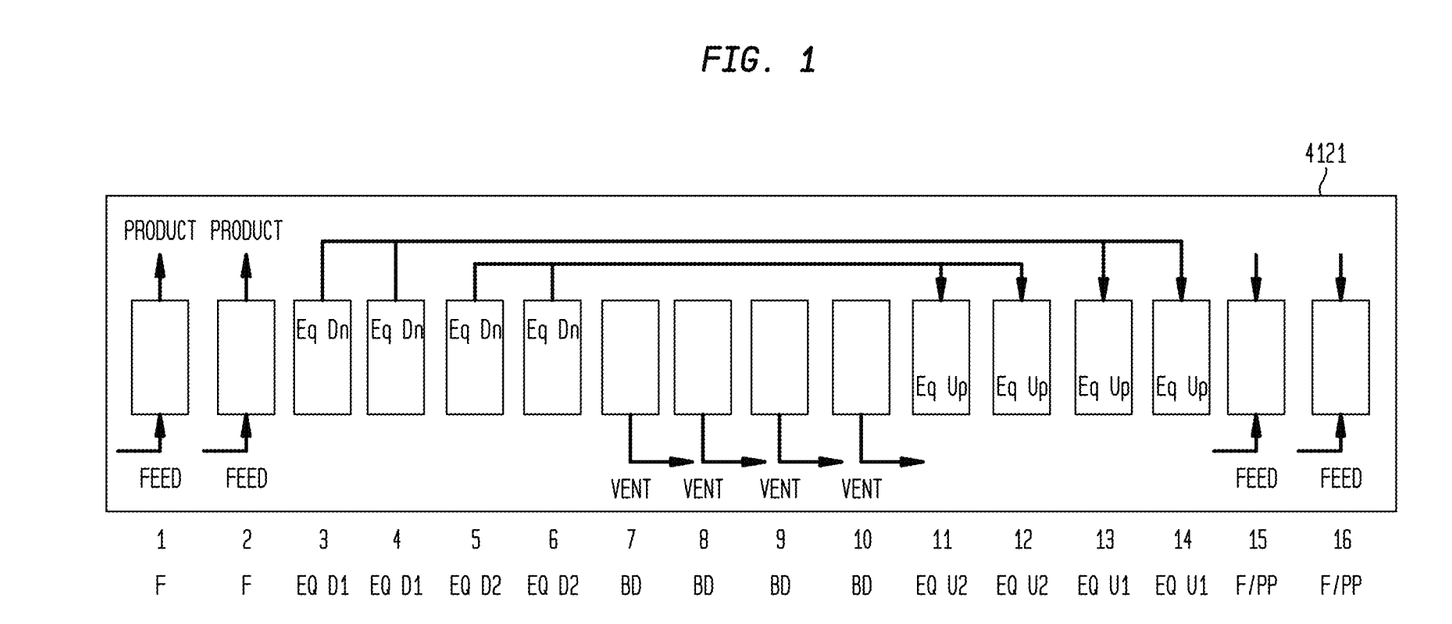
FIG. 1 shows the process for a 4131 cycle from the view of a single bed.
Figure 2:
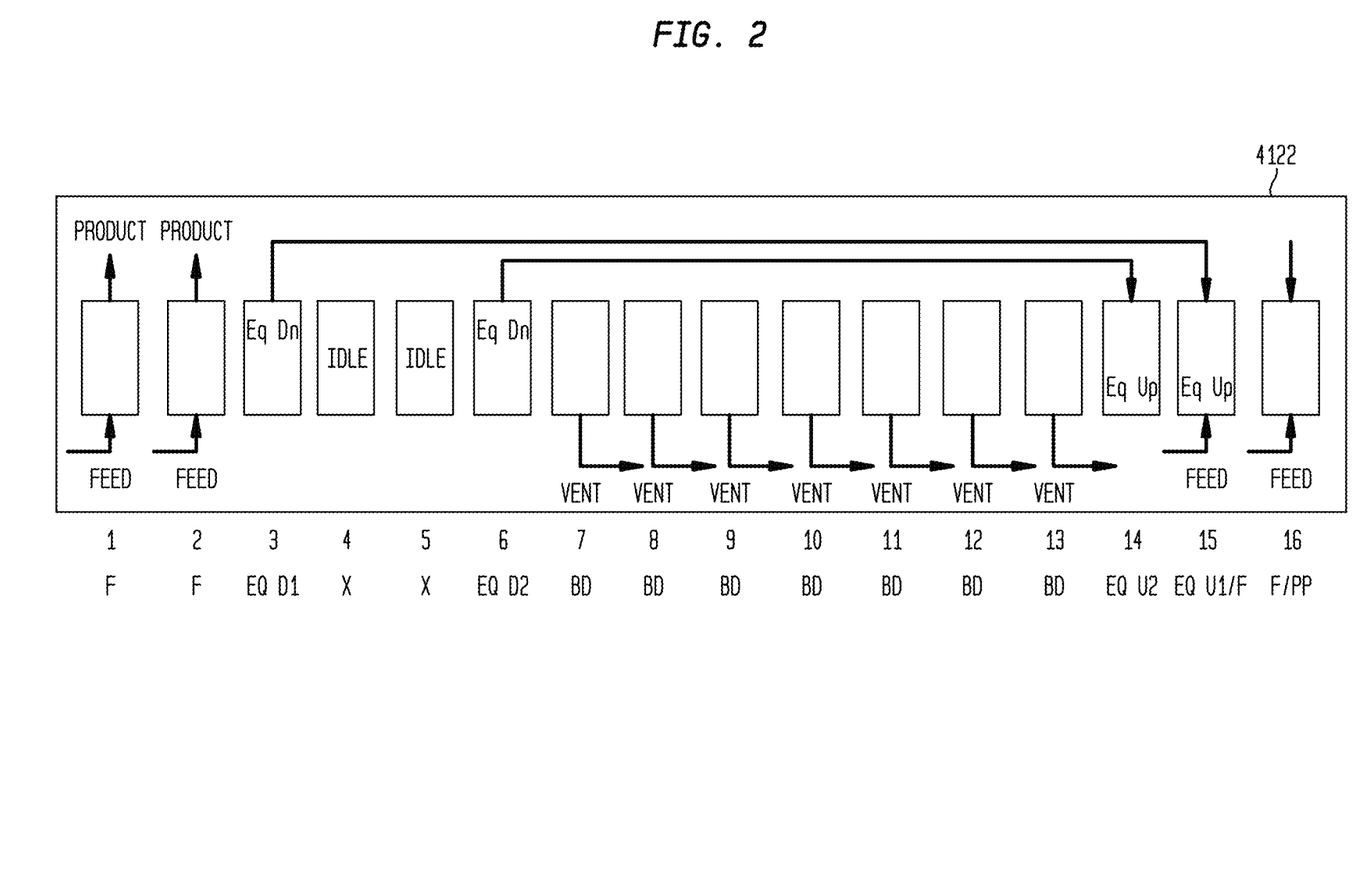
FIG. 2 shows the process for a 4122 cycle from the view of a single bed.
Figure 3:
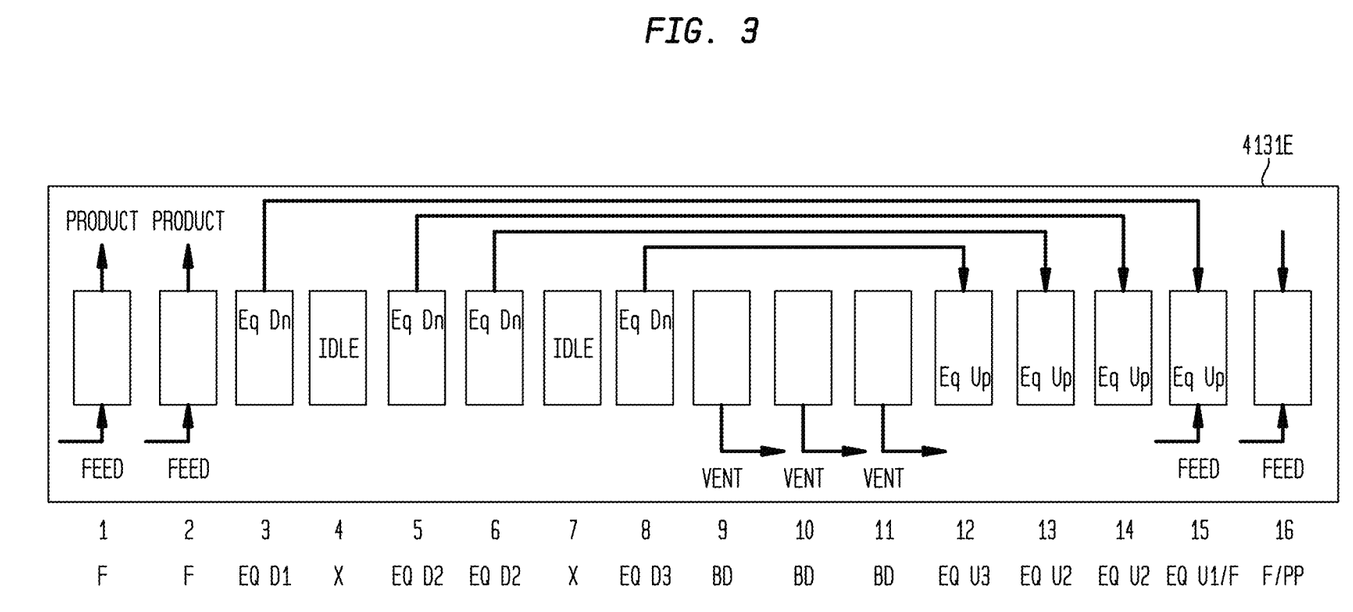
FIG. 3 shows the process for a 4221 cycle from the view of a single bed.
Figure 9:
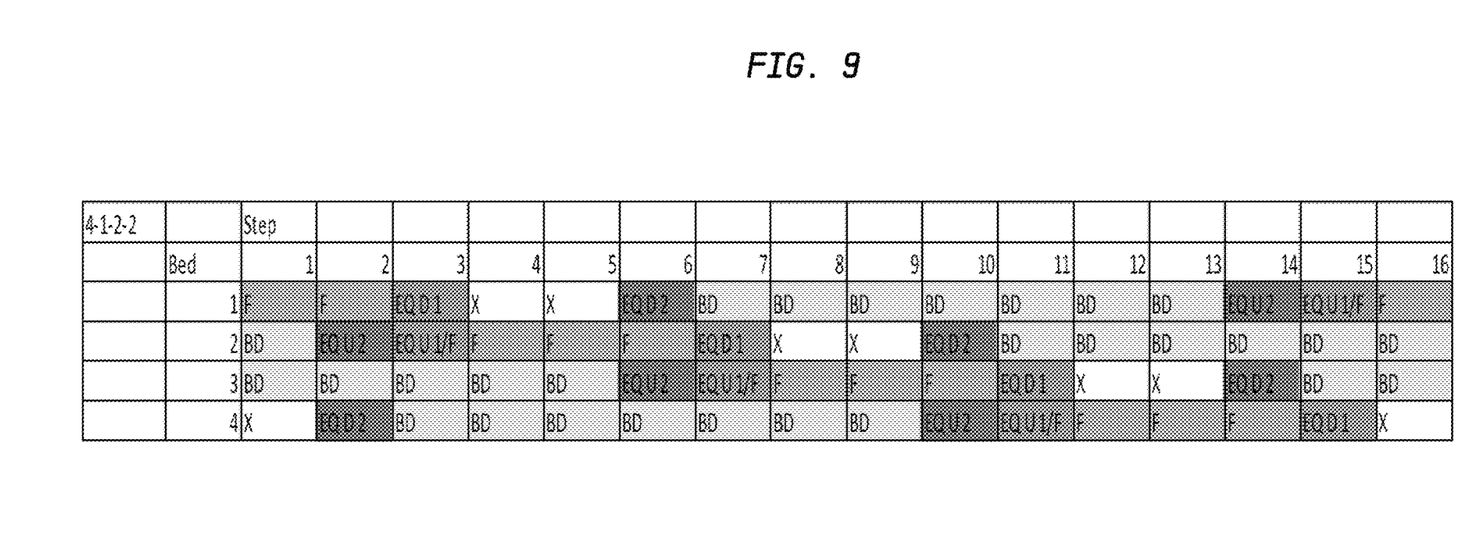
FIG. 9 shows the cycle chart for a 4122 cycle.
Figure 10:
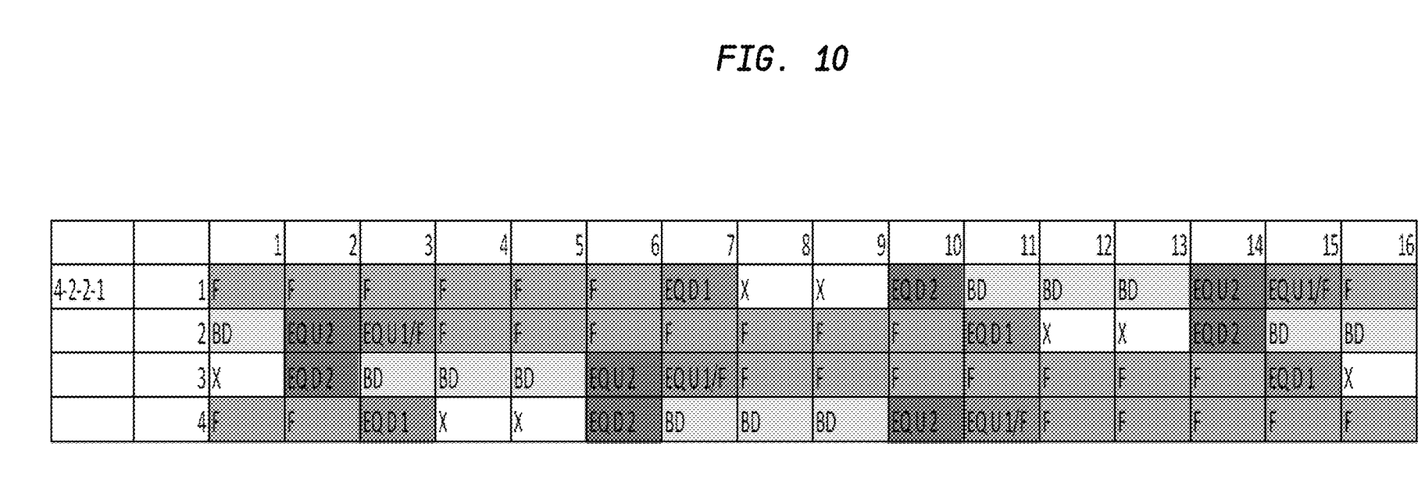
FIG. 10 shows the cycle chart for a 4221 cycle.

The principles of the invention can be summarized as follows:
1. A process that has a at least 2 beds in service where there exists a feed step to the bed, a product make step that overlaps with feeding the bed, at least one equalization up step and one equalization down step, a blow down step to depressurize the bed and one or more of the following characteristics:

a. Substantially no purge provided to the bed in blow down
b. Very rapid equalization steps of 10 seconds or less, preferably 6 seconds or less, but generally greater than 1 second
c. Overlapping of the feed pressurization and an equalization up step
d. A rest step where the bed is isolated from all gas streams Specific examples of optimal combinations of these findings are the 4-1-3 cycle, the 4-1-2 cycle and the 4-2-2 cycle for 4 bed systems. A 4-1-3 cycle is presented in FIG. 1 and the cycle chart in FIG. 8. A 4-1-2 cycle is present in FIG. 2 and a cycle chart in FIG. 9. A 4-2-2 cycle is presented in FIG. 3 and a cycle chart in FIG. 10.

While these characteristics are primarily described for the separation of nitrogen from natural gas, it should be noted that they will apply to other kinetic based separations as well provided that there exists a kinetic basis for the separation of at least one of the gases from the feed stream. Layering schemes of multiple adsorbents exist for which this process can be applied.

Modeling Description

The results from the breakthrough test and parameters obtained from the modeling were used with the methodology described by Mehrotra, et al. in Arithmetic Approach for Complex PSA Cycle Scheduling, Adsorption, 2010, pp. 113-126, vol. 16, Springer Science+Business Media which details the basis for modeling PSA processes. These simulations were performed using Process Builder, from PSE.

Pilot Description

The pilot system is a pressure swing adsorption system that operates by exploiting the difference in adsorption capacity of an adsorbent for the gas of interest over a specific pressure range. When the vessel containing the adsorbent is pressurized, the adsorbent will selectively adsorb the contaminant from the gas stream and thus remove it from the product stream that exits through the other end of the vessel. When vessel is depressurized, the contaminant will desorb and the adsorbent will be ready to process the feed stream again. This process is made into a semi-continuous batch process by having 1 vessel or more than 1 vessel available to process the gas at the majority of all times. With more than 1 vessel to process gas, additional options are available to further increase efficiency by retaining pressurized gas in dead volume spaces (piping or the heads of the vessels) and the process then has the ability to generate a continuous stream of product.

Figure 7:
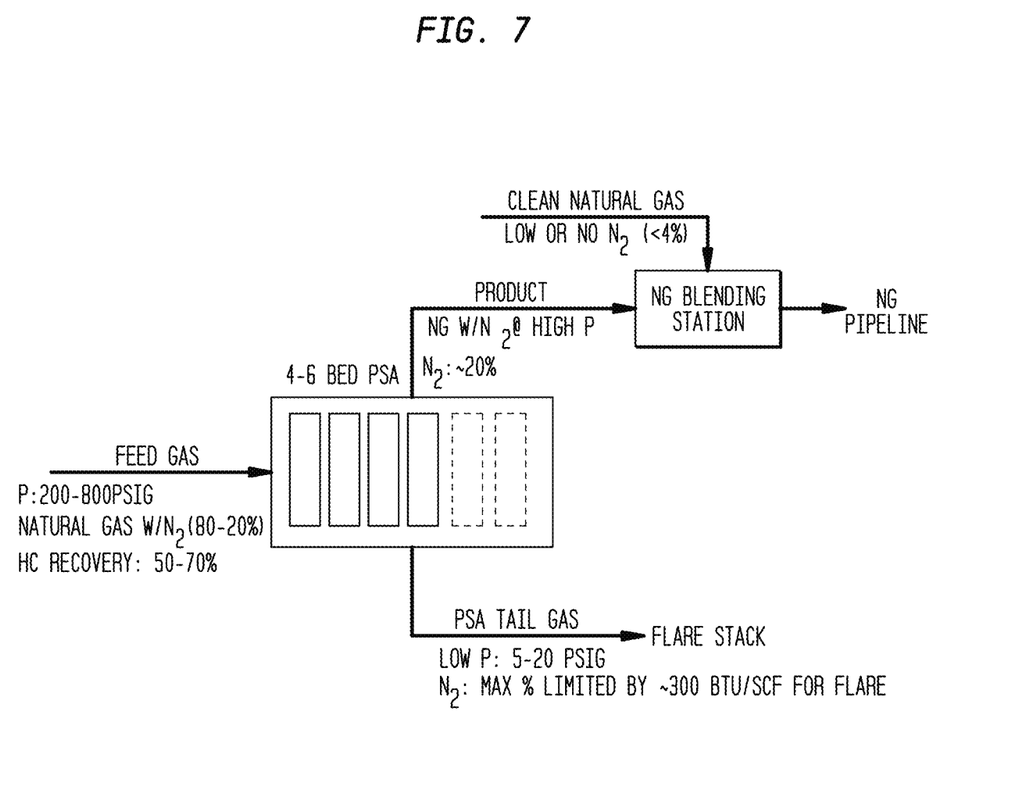
FIG. 7 shows a diagram showing a typical application of this system to a natural gas well head feed stream, post hydraulic fracturing.

The conceptual process flow diagram is presented in FIG. 7.

The pilot system employs multiple PSA vessels to achieve the desired nitrogen rejection and hydrocarbon recovery target. The current pilot PSA design consists of 4-6 vessels with process steps consisting of 1 bed on feed and 1 bed on blowdown at a time. There are 2-3 equalization steps as well as product pressurization and purge steps. The pilot system was designed to process up to 17 kscfd and capable of using 1 to 4 inch diameter beds. During the initial construction of the pilot test system the bed size was selected to be 1 inch due to the adsorbent performance and with considerations of adsorbent manufacturing. The height was based on maximum available height in the container. The remaining components of the design were based on similar 6 bed PSA pilot plant already in operation. Full range control valves were used for all valves. The system was constructed entirely of stainless steel grade 316. Additionally, a pretreatment system of 304 stainless steel was designed and built as $H_2S$ compatible in order to remove all condensed liquids and sulfur before entering the PSA portion of the system.

TGA Description

Figure 4:
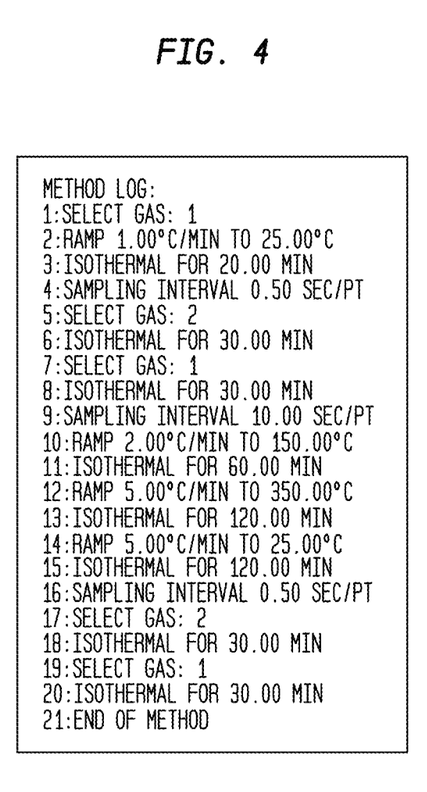

Routine characterization (method in FIG. 4) of modified 4A samples was performed using a thermogravimetric method using a TA Instruments Q500 system installed in a glove box to minimize the impact of air leaks. Nitrogen and oxygen gases supplied to the instrument were high purity. The balance purge gas and gas 1 was nitrogen and a gas 2 corresponds to oxygen. For all experiments, a balance purge of 5 cc/minute was used and the gas directly over the sample was set to 95 cc/minute (nitrogen or oxygen). A sampling frequency of 0.5 sec/point was used for all adsorption steps. Alumina pans were used for all studies and the sample size after activation was in the range 100 to 120 mg.

Figure 5:
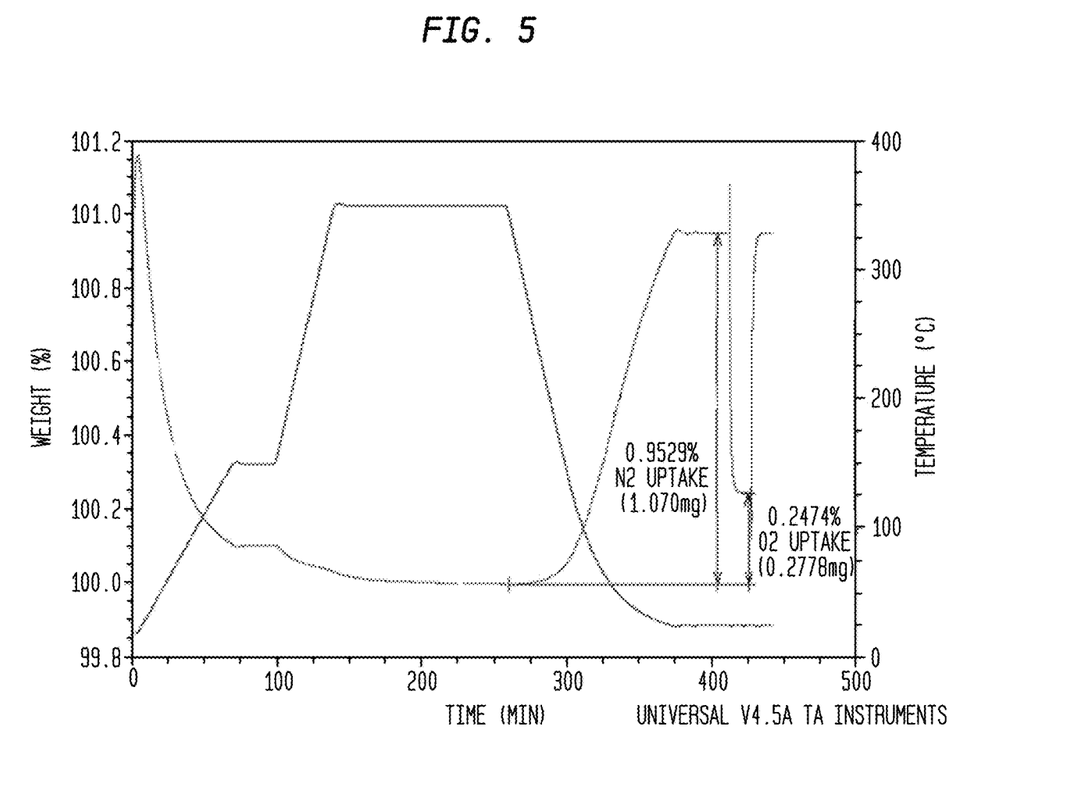
FIG. 5 shows an example of a TGA plot that is obtained following the method outlined in FIG. 4.
Figure 6:
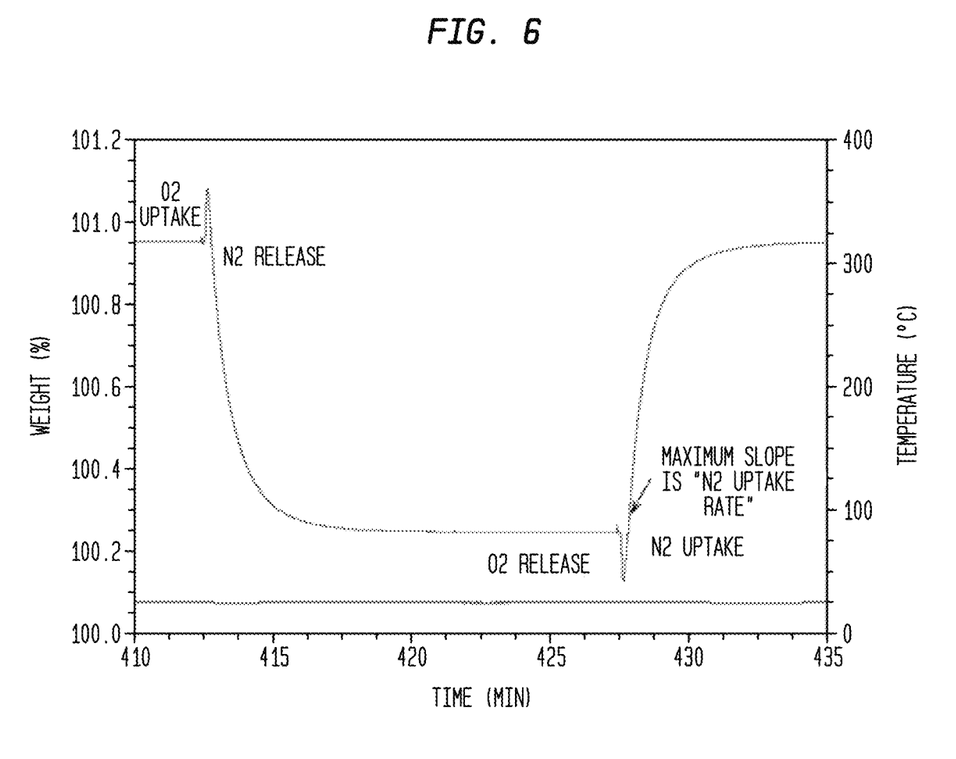
FIG. 6 shows an expansion of the same plot in FIG. 3 to illustrate the features observed during gas switching.

The TGA method involves both an in-situ activation step followed by adsorption tests using oxygen and nitrogen at 25° C. The sample activation was performed by heating the sample under nitrogen purge at 2° C. per minute to 150° C., maintaining isothermal for 60 minutes, heating at 5° C./minute to 350° C., holding at 350° C. for 120 minutes, then cooling to 25° C. The nitrogen equilibrium capacity at atmospheric pressure and 25° C. is reported as the weight gain on cooling under nitrogen relative to the minimum weight at 350° C. (the activated sample weight). An assessment of relative rate for different samples and preparation is captured by switching from nitrogen to oxygen. A transient weight gain is observed followed by a drop attributable to oxygen uptake followed by nitrogen leaving. A corresponding switch from oxygen back to nitrogen results in a transient weight loss followed by a weight gain attributable to oxygen loss followed by nitrogen pickup. Values reported as "nitrogen uptake rate" correspond to the maximum slope observed in the nitrogen uptake portion and is equivalent also to the peak in the derivative weight with respect to time for the same step as shown in FIGS. 5 and 6. Values are reported in weight %/minute.

Example 1

A material was made to demonstrate the proposed benefit of cycle changes in a pilot system as described earlier.

23.00 lbs. of zeolite 4A powder on a dry weight basis (29.50 lbs. wet weight) was placed in a WAM MLH50 plow mixer. With the mixer agitating, 2.16 lbs of MR-2404 (a solventless silicone containing silicone resin from Dow Corning) was pumped in at rate of 0.07 lb/min. After the MR-2404 addition was completed, 9.2 lbs of water was added at a rate of 0.3 lb/min under constant stirring in the plow mixer. At the end of the water addition, plow mixing was continued for an additional 5 minutes. The plow mixed powder product labeled hereinafter "the formulation" was transferred to a tilted rotating drum mixer having internal working volume of ~75 L and agitated therein at a speed of 24 rpm. Mixing of the formulation was continued while beads were gradually formed which had a porosity, as measured using a Micromeritics Autopore IV Hg porosimeter on the calcined product, in the 30-35% range. The beads were subjected to a screening operation to determine the yield and harvest those particles in the 8×16 U.S. mesh size range. The product beads were air dried overnight prior to calcination using a shallow tray method at temperatures up to 595° C. The shallow tray calcination method used a General Signal Company Blue-M electric oven equipped with a dry air purge. ~500 g. dry wt. of the 8×16 U.S. mesh adsorbent was spread out in a stainless steel mesh tray to provide a thin layer. A purge of 200 SCFH of dry air was fed to the oven during calcination. The temperature was set to 90° C., followed by a 6 hour dwell time. The temperature was then increased to 200° C. gradually over the course of a 6 hour period, and further increased to 300° C. over a 2 hour period and finally increased to 595° C. over a 3 hour period and held there for 1 hour before cooling to 450° C. after which the adsorbent was removed, immediately bottled in a sealed bottle and placed in a dry nitrogen purged drybox. The calcined beads were rescreened to harvest those particles in the 8×16 U.S. mesh range.

Characterization of the modified 4A samples calcined at 595° C. was performed using a thermogravimetric method as described earlier in "ANRU TGA Testing". The nitrogen uptake rate as performed in the test was determined to be ~0.2 weight %/minute as measured using the TGA method disclosed herein. When the product beads in Example 1 were calcined up to 575° C., the nitrogen uptake rate as performed in the test was determined to be ~0.7 weight %/minute as measured using the TGA method disclosed herein. Subsequently, when the product beads in Example 1 were calcined up to 555° C., the nitrogen uptake rate as performed in the test was determined to be ~1.2 weight %/minute as measured using the TGA method disclosed herein.

With this material and with modeling results to confirm, results were generated detailing the benefit of each of the four specifications for the process cycle. The first change of eliminating purge showed a substantial increase in the model predicted recovery and the ability of the pilot system to overcome the void space losses and begin making a product. This demonstrates the viability and benefit of eliminating purge. The next change was the introduction of rest steps which enabled the addition of a $3^{rd}$ equalization step. This $3^{rd}$ equalization step substantially reduced void space losses in both the model and the pilot. This demonstrates the substantial benefit of adding a rest step in this process. The third changes is in the introduction of an overlapping feed and equalization step. This enabled the process to reduce the feed velocity inside the bed and enabled the process to substantially increase recovery in both the model and pilot. Last was the reduction in equalization step times from 10 s to 2-4 seconds. This final change resulted in additional benefit as can be seen in the table. What is especially critical to note here is that the state-of-the-art processes in the field teach a process that would result in essentially no demonstratable processing capability of this adsorbent in a commercial or pilot system and even the addition of one or two of these steps would give the apparent result that the material does not perform the separation. It is only with the insight of the modeling environment and substantial work carefully tuning the pilot control process to adjust to the adsorbent that the process is able to demonstrate any success at all. This process is a series of four directly counter violations to the teachings of kinetic process cycles and equilibrium cycles in the literature.

Figure 8:
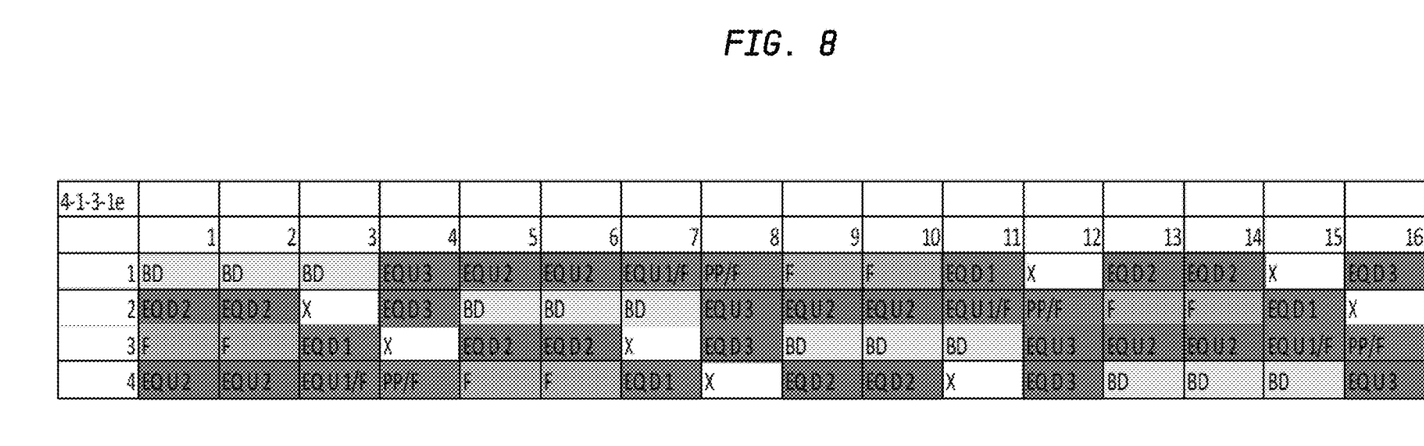
FIG. 8 shows the cycle chart for a 4131 cycle.

A 4-1-3-1 cycle chart is depicted in FIG. 8 showing the steps that each bed progresses through. This is a substantially different cycle chart than the state of the art as a $3^{rd}$ equalization is present in a 4 bed system that does not contain an equalization tank. The cycle chart depicted in FIG. 9, the 4-1-2-2 cycle, has substantially longer blowdown times and the cycle chart in FIG. 10, the 4-2-2-1 cycle, has double the beds on feed than what is conventionally taught possible with 4 beds and two equalizations.

TABLE 1

Performance of various cycles

| Overlap Feed | Beds | Feed | Eqs | Vent | Purge/Feed | Model Recovery* | Pilot Recovery** | Eq step time | Model Feed* | Pilot Feed** |
|---|---|---|---|---|---|---|---|---|---|---|
| None | 4 | 1 | 2 | 1 | 0.1 | 8.2% | 0% | 10 s | 100% | 100% |
| None | 4 | 1 | 2 | 1 | <0.01 | 21.1% | 2% | 10 s | 100% | 100% |
| None | 4 | 1 | 3 | 1 | <0.01 | 39.9% | 6% | 10 s | 100% | 100% |
| Overlap | 4 | 1 | 3 | 1 | <0.01 | 66.2% | 20% | 10 s | 104% | 110% |
| Overlap | 4 | 1 | 3 | 1 | <0.01 | 84.1% | 34% | 2-4 s | 106% | 120% |

*35% $N_2$ in $CH_4$ feed, 10% $N_2$ in product, variable feed flow, feed pressure 410 psig, product pressure 405 psig
**32-36% $N_2$ in pipeline sales natural gas feed, 18-21% $N_2$ in product, variable feed flow, feed pressure 380-405 psig, product pressure 375-400 psig
Adding a rest step enabled the additional $3^{rd}$ equalization to the process.

Example 2. Shorter Equalizations Further Examined

Equalization Time Effect (Graph)

Figure 11:
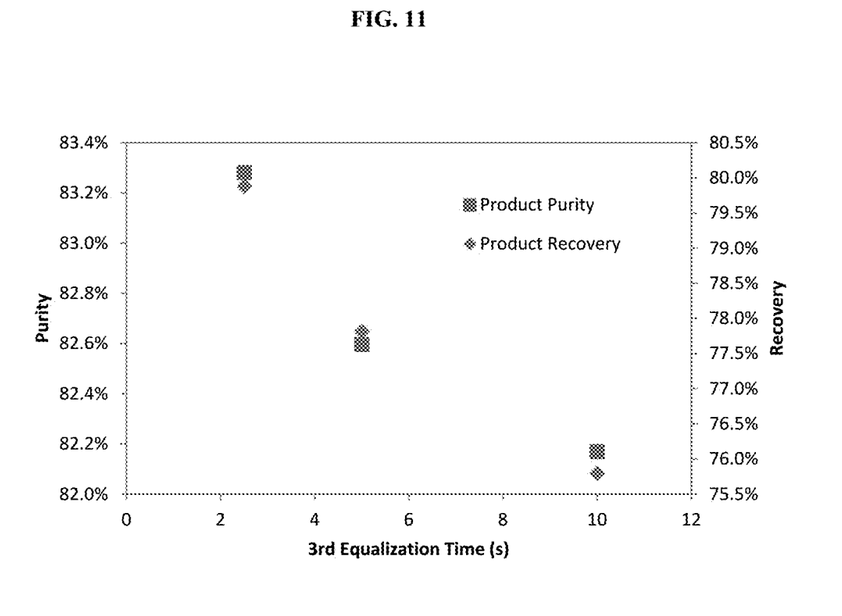
FIG. 11 shows the benefit of decreasing equalization times on the purity and recovery of the system.

A model was created to show the benefit of decreasing equalization times on the purity and recovery of the system and substituting a rest step for the remainder of the equalization time. As shown in FIG. 11, the increases here are substantial and worth noting, the increase in processed flow is substantially more impressive when the rest step is exchanged for an additional feed step or an additional blow down step.

We claim:
1. A pressure swing adsorption process for separating a pressurized feed supply gas containing at least one more rapidly adsorbable component and at least one less rapidly adsorbable product gas component which comprises continuous feeding of a supply gas into a feed input end of an adsorber bed containing at least one solid adsorbent which kinetically adsorbs the more rapidly adsorbable component and withdrawing the least rapidly adsorbable component from an exit end of the adsorber bed, which has at least 2 beds in service in which the continuous feeding of the supply gas sequentially through each of the adsorber beds produces product gas by using continuous feed gas, a constant product gas step, a product pressurization step, a high pressure equalization step, a product make step that overlaps with feeding the bed, at least one equalization up step and at least one low pressure equalization down step, a blow down step to depressurize the bed, wherein there is no purge provided to any bed during any step in the PSA process.

2. The process of claim 1 wherein the equalization steps are conducted in 10 seconds or less.

3. The process of claim 1 wherein feed pressurization overlaps with the last equalization up step.

4. The process of claim 1 wherein there is at least one rest step where a bed in the process is isolated from all gas streams.

5. The pressure swing adsorption process of claim 1 wherein the less rapidly adsorbable component is the product gas comprising methane and the more rapidly adsorbable component is $N_2$ and/or $CO_2$.

6. The pressure swing adsorption process of claim 1 wherein the less rapidly adsorbable component is the product gas which comprises $N_2$ and the more rapidly adsorbable component is $O_2$.

7. The pressure swing adsorption process of claim 1 wherein each adsorption bed contains zeolitic material.

8. The process of claim 1 wherein there are very rapid equalization steps of 10 seconds or less.

9. The process of claim 8 wherein the cycle has overlapping feed pressurization and the last equalization up step.

10. The process of claim 8 wherein there is at least one rest step where the bed is isolated from all gas streams.

11. The process of claim 1 wherein said adsorbent comprises zeolite A, chabazite, mordenite, clinoptilolite, ZSM-5, or combinations thereof.

12. The process of claim 11 wherein said adsorbent is a zeolite exchanged with at least one cation selected from Li, Na, K, Mg, Ca, Sr, Ba, Cu, Ag, Zn, NH4+ and combinations or mixtures thereof.

13. A pressure swing adsorption process for separating a pressurized feed supply gas containing $N_2$ and methane which comprises continuous feeding said supply gas into a feed input end of an adsorber bed containing at least one solid adsorbent which kinetically adsorbs $N_2$ and withdrawing the methane having a reduced amount of $N_2$ from an exit end of the adsorber bed, which has at least 2 beds in service in which the continuous feeding of the supply gas sequentially through each of the adsorber beds produces product methane gas by using continuous feed gas, a constant product gas step, a product pressurization step, a high pressure equalization step, a product make step that overlaps with feeding the bed, at least one equalization up step and at least one low pressure equalization down step, a blow down step to depressurize the bed, wherein there is substantially no purge provided to any bed during any step in the PSA process.

14. The process of claim 13 wherein the equalization steps are conducted in 10 seconds or less.

15. The process of claim 13 wherein feed pressurization overlaps with the last equalization up step.

16. The process of claim 13 wherein there is at least one rest step where a bed in the process is isolated from all gas streams.

17. A pressure swing adsorption process for separating a pressurized feed supply gas containing at least one more rapidly adsorbable component and at least one less rapidly adsorbable product gas component in a four bed system which comprises the continuous feeding of a supply gas into a feed input end of an adsorber bed containing at least one solid adsorbent which preferentially adsorbs the more rapidly adsorbable component and withdrawing the least rapidly adsorbable product gas component from an exit end of the adsorber bed in a sixteen-step cycle following the cycle chart:

| | 4-1-3-1e | | | | | | |
|---|---|---|---|---|---|---|---|
| 1 | 2 | 3 | 4 | 5 | 6 | 7 | 8 |
| 1 BD | BD | BD | EQU3 | EQU2 | EQU2 | EQU1/F | PP/F |
| 2 EQD2 | EQD2 | X | EQD3 | BD | BD | BD | EQU3 |
| 3 F | F | EQD1 | X | EQD2 | EQD2 | XD | EQD3 |
| 4 EQU2 | EQU2 | EQU1/F | PP/F | F | F | EQD1 | X |
| 9 | 10 | 11 | 12 | 13 | 14 | 15 | 16 |
| 1 F | F | EQD1 | X | EQD2 | EQD2 | X | EQD3 |
| 2 EQU2 | EQU2 | EQU1/F | PP/F | F | F | EQD1 | X |
| 3 BD | BD | BD | EQU3 | EQU2 | EQU2 | EQU1/F | PP/F |
| 4 EQD2 | EQD2 | X | EQD3 | BD | BD | BD | EQU3 | wherein:

F—feed step and make product if at pressure

EQD1—first equalization down

EQD2—second equalization down

EQD3—third equalization down

X—Idle step

BD—bed blow down/vent

EQU3—third equalization up

EQU2—second equalization up

EQU1/F—first equalization up, overlap feed

PP/F—product pressurization, overlap feed.

18. A pressure swing adsorption process for separating a pressurized feed supply gas containing at least one more rapidly adsorbable component and at least one less rapidly adsorbable product gas component in a four bed system which comprises the continuous feeding of a supply gas into a feed input end of an adsorber bed containing at least one solid adsorbent which preferentially adsorbs the more rapidly adsorbable component and withdrawing the least rapidly adsorbable product gas component from an exit end of the adsorber bed in a sixteen-step cycle following the cycle chart:

| 4-1-2-2 | | | | | | | | | | | | | | | | |
|---|---|---|---|---|---|---|---|---|---|---|---|---|---|---|---|---|
| Step<br>Bed | 1 | 2 | 3 | 4 | 5 | 6 | 7 | 8 | 9 | 10 | 11 | 12 | 13 | 14 | 15 | 16 |
| 1 | F | F | EQD1 | X | X | EQD2 | BD | BD | BD | BD | BD | BD | BD | EQU2 | EQU1/F | F |
| 2 | BD | EQU2 | EQU1/F | F | F | F | EQD1 | X | X | EQD2 | BD | BD | BD | BD | BD | BD |
| 3 | BD | BD | BD | BD | BD | EQU2 | EQU1/F | F | F | F | EQD1 | X | X | EQD2 | BD | BD |
| 4 | X | EQD2 | BD | BD | BD | BD | BD | BD | BD | EQU2 | EQU1/F | F | F | F | EQD1 | X | wherein:
F—feed step and make product if at pressure
EQD1—first equalization down
EQD2—second equalization down
EQD3—third equalization down
X—Idle step
BD—bed blow down/vent
EQU3—third equalization up
EQU2—second equalization up
EQU1/F—first equalization up, overlap feed
PP/F—product pressurization, overlap feed.

19. A pressure swing adsorption process for separating a pressurized feed supply gas containing at least one more rapidly adsorbable component and at least one less rapidly adsorbable product gas component in a four bed system which comprises the continuous feeding of a supply gas into a feed input end of an adsorber bed containing at least one solid adsorbent which preferentially adsorbs the more rapidly adsorbable component and withdrawing the least rapidly adsorbable product gas component from an exit end of the adsorber bed in a sixteen-step cycle following the cycle chart:

| 4-2-2-1 | | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 1 | F | F | F | F | F | F | EQD1 | X | X | EQD2 | BD | BD | BD | EQU2 | EQU1/F | F |
| 2 | BD | EQU2 | EQU1/F | F | F | F | F | F | F | F | EQD1 | X | X | EQD2 | BD | BD |
| 3 | X | EQD2 | BD | BD | BD | EQU2 | EQ1/F | F | F | F | F | F | F | F | EQD1 | X |
| 4 | F | F | EQD1 | X | X | EQD2 | BD | BD | BD | EQU2 | EQU1/F | F | F | F | F | F | wherein:
F—feed step and make product if at pressure
EQD1—first equalization down
EQD2—second equalization down
EQD3—third equalization down
X—Idle step
BD—bed blow down/vent
EQU3—third equalization up
EQU2—second equalization up
EQU1/F—first equalization up, overlap feed
PP/F—product pressurization, overlap feed.

\* \* \* \* \*